United States Patent

Hardy

[11] 4,046,736
[45] Sept. 6, 1977

[54] 1,3-BIS[(2,2,6,6-TETRAALKYL-4-PIPERIDYLIDENE)AMINO]GUANIDINES AS LIGHT STABILIZERS FOR POLYOLEFINS

[75] Inventor: William Baptist Hardy, Bound Brook, N.J.

[73] Assignee: American Cyanamid Company, Stamford, Conn.

[21] Appl. No.: 715,019

[22] Filed: Aug. 16, 1976

[51] Int. Cl.$^2$ .................................................. C07D 401/12
[52] U.S. Cl. ............................ 260/45.8 N; 260/293.63
[58] Field of Search ..................... 260/293.63, 45.8 N

[56] References Cited

U.S. PATENT DOCUMENTS

| | | | |
|---|---|---|---|
| 3,734,883 | 5/1973 | Holt | 260/293.63 |
| 3,828,052 | 8/1974 | Holt et al. | 260/293.63 |

*Primary Examiner*—Henry R. Jiles
*Assistant Examiner*—Robert T. Bond
*Attorney, Agent, or Firm*—Philip Mintz

[57] ABSTRACT

Compounds of the formula:

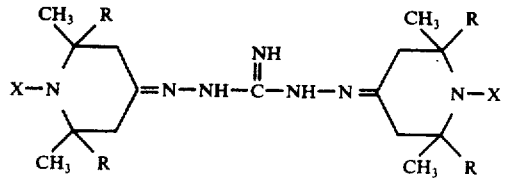

wherein X is —H, —OH, —O. alkyl of 1 to 8 carbon atoms, or acyl of 2 to 10 carbon atoms, and R is alkyl of 1 to 8 carbon atoms are useful for stabilizing polyolefins against degradation by ultraviolet light.

13 Claims, No Drawings

1,3-BIS[(2,2,6,6-TETRAALKYL-4-PIPERIDYLIDENE)AMINO]GUANIDINES AS LIGHT STABILIZERS FOR POLYOLEFINS

This invention relates to certain novel compounds and to their use as light stabilizers for polyolefins. More particularly this invention relates to novel compounds of the formula (I):

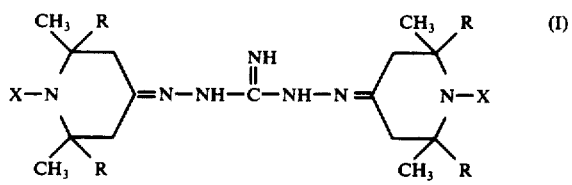

wherein X is —H, —OH, —O., alkyl of 1 to 8 carbon atoms or acyl of 2 to 10 carbon atoms and R is alkyl of 1 to 8 carbon atoms and to the use of such compounds for stabilizing polyolefins, particularly polypropylene, against degradation by ultraviolet radiation.

It is well known that sunlight and other sources of ultraviolet radiation cause degradation of polymers as evidenced by embrittlement or yellowing of plastic articles made therefrom. It is also well known that this degradation can be inhibited by use of ultraviolet light stabilizers incorporated in or on such articles. Various additives, used alone or in combinations have been suggested to inhibit such light degradation in order to prolong the useful lives of articles made from polyolefins. Since none has been found to be completely satisfactory, research continues in order to find compounds or combinations of compounds which will be more satisfactory. The present invention arose out of such research and resulted in the discovery of novel compounds which stabilize polyolefins against degradation by ultraviolet light.

In accordance with the present invention, I have discovered that the above-described compounds of formula (I) provide effective stabilization of polyolefins against deterioration by ultraviolet radiation. They are particularly useful in stabilizing polypropylene. These compounds may be incorporated in or on such plastic materials by any of the various procedures known in the art for such purpose, such as by dry blending the additive with the polyolefin in powder or granular form followed by milling, Banbury mixing, molding, casting, extruding, swelling, and the like; by immersing the polyolefin as film, sheet, fibers, etc. in a solution of the additive in an appropriate solvent (as in a dyeing process), etc.

The amount of the compound of formula (I), needed to be an effective amount for stabilizing the polyolefin against degradation will depend on the nature of the polyolefin and the amount of exposure to ultraviolet light to which the article will be subjected. For most purposes it is sufficient to use an amount of the compound of formula (I) within the range of about 0.1 to about 5 percent by weight, preferably 0.2 to 2 percent by weight, based on the weight of untreated polyolefin.

The compounds of formula (I) can be prepared by reacting two moles of the appropriate 4-piperidone of formula (II) with one mole of diaminoguanidine hydrochloride of formula (III) to produce the corresponding 1,3-bis[(2,2,6,6-tetraalkyl-4-piperidylidene)amino]guanidine hydrochloride of formula (IV), which can be neutralized with alkali to produce the desired free base as illustrated by the following reactions:

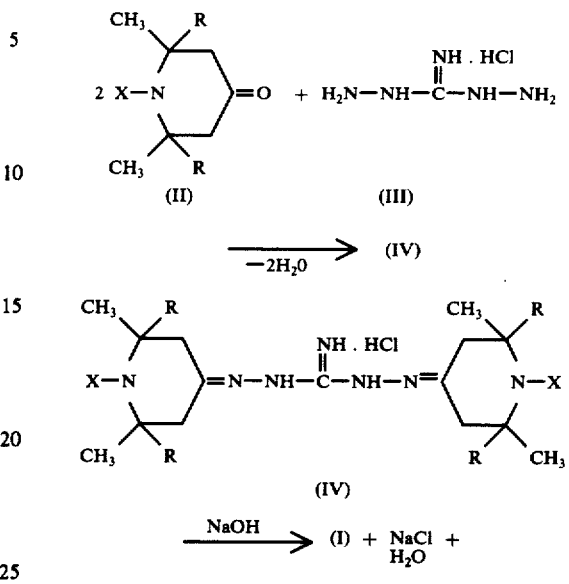

wherein X and R are as previously defined.

Suitable 4-piperidones which can be used in this reaction include the following: 2,2,6,6-tetramethyl-4-piperidone; 1,2,2,6,6-pentamethyl-4-piperidone; 1-ethyl-2,2,6,6-tetramethyl-4-piperidone; 1-n-octyl-2,2,6,6-tetramethyl-4-piperidone; 2,6-diethyl-2,6-dimethyl-4-piperidone; 2-isobutyl-2,6,6-trimethyl-4-piperidone; 1-acetyl-2,2,6,6-tetramethyl-4-piperidone; 1-benzoyl-2,2,6,6-tetramethyl-4-piperidone; 1-hydroxy-2,2,6,6-tetramethyl-4-piperidone; 1-oxyl-2,2,6,6-tetramethyl-4-piperidone; and the like.

Many of the compounds of formula (II) are known compounds. The preparations, many of them can be found in such literature, for example, as Francis, J. Chem. Soc., 2897 (1927) for the preparation of triacetonamine, another name for 2,2,6,6-tetramethyl-4-piperidone (where X is —H); Biel & Robertson, U.S. Pat. No. 3,364,220, Example 9, for the preparation of 1,2,2,6,6-pentamethyl-4-piperidone (where X is methyl); Rozantsev and Golubev, Chem. Abs. 65, 10559e (1966), for the preparation of 1-hydroxy-2,2,6,6-tetramethyl-4-piperidone (where X is —OH); Nieman, Rozantzer, & Mamedova, Nature 196, 472 (1962), for the preparation of triacetoamine-N-oxide, another name for 1-oxyl-2,2,6,6-tetramethyl-4-piperidone (where X is —O.) and the hydroxylamine derivative, 1-hydroxy-2,2,6,6-tetramethyl-4-piperidone (where X is —OH); and Holt, U.S. Pat. No. 3,734,883, column 2 lines 1-18, for the preparation of these compounds where X is —O. or methyl. Other compounds within the scope of formula (II) can be prepared similarly.

Illustrative of the compounds represented by formula (I) are: 1,3-bis[(2,2,6,6-tetramethyl-4-piperidylidene)amino]guanidine; 1,3-bis[(1,2,2,6,6-pentamethyl-4-piperidylidene)amino]guanidine; 1,3-bis[(1-ethyl-2,2,6,6-tetramethyl-4-piperidylidene)amino]guanidine; 1,3-bis[(1-n-octyl-2,2,6,6-tetramethyl-4-piperidylidene)amino]guanidine; 1,3-bis[(2-isobutyl-2,6,6-trimethyl-4-piperidylidene)amino]-guanidine; 1,3-bis[(1-acetyl-2,2,6,6-tetramethyl-4-piperidylidene)amino]guanidine; 1,3-bis[(1-benzoyl-2,2,6,6-tetramethyl-4-piperidylidene)amino]guanidine;

1,3-bis[(1-hydroxy-2,2,6,6-tetramethyl-4-piperidylidene)amino]guanidine; 1,3-bis[(1-oxyl-2,2,6,6-tetramethyl-4-piperidylidene)amino]-guanidine; 1,3-bis[(2,6-diethyl-2,6-dimethyl-4-piperidylidene)amino]-guanidine; and the like.

The compounds of formula (I) may be used in the polyolefin alone or in combination with other additives, such as fillers, antioxidants, flame retardants, heat stabilizers, anti-slipping and anti-static agents, supplemental light stabilizers, pigments, dyes, lubricants, etc.

As with the compound of formula (I), any further additive is advantageously employed in a proportion within the range of from about 0.1 to about 5 percent by weight, preferably 0.2 percent to 2 percent by weight, based on the weight of untreated polyolefin.

Illustrative of suitable antioxidants are those of the hindered-phenol type, such as 2,6-di-t-butyl-p-cresol; 4,4'-bis(2,6-di-t-butylphenol); 4,4'-bis(2,6-di-iso-propylphenol); 2,4,6-tri-t-butylphenol; 2,2'-thiobis(4-methyl-6-t-butylphenol); octadecyl 2(3',5'-di-t-butyl-4'-hydroxyphenyl)-propionate; etc.; esters of thiodipropionic acid, such as dilauryl thiodipropionate and distearyl thiodipropionate, etc.; hydrocarbyl phosphites, such as triphenyl phosphite, trinonyl phosphite, diphenyldecyl phosphite, etc.; and combinations thereof.

Illustrative of the supplemental light stabilizers are those of the benzotriazole class, such as 2-(2'-hydroxy-5'-octylphenyl) benzotriazole; 2-[2'-hydroxy-3',5'-di-t-butylphenyl)-5-chlorobenzotriazole; those of the hydroxybenzophenone type, such as 2-hydroxy-4-methoxybenzophenone; 2-hydroxy-4-octyloxybenzophenone; 2,2'-dihydroxy-4,4'-dimethoxybenzophenone; hindered phenol esters, such as 2',4'-di-t-butylphenyl 3,5-di-t-butyl-4-hydroxybenzoate; metal complexes, such as nickel complexes of 2,2'-thiobis(4-6-octylphenol); nickel butylamine complex of 2,2'-thiobis(4-t-octylphenol); nickel complexes of bis(4-t-octylphenyl)sulfone; nickel dibutyl dithiocarbamate; nickel salts of 4-hydroxy-3,5-di-t-butylbenzyl phosphonic acid monoalkyl esters where alkyl is methyl, ethyl, propyl, butyl, etc.; nickel complex of 2-hydroxy-4-methylphenyl undecyl ketone oxime; etc. Further illustrative examples of suitable antioxidants and of suitable supplemental light stabilizers can be found in columns 3 and 4 of U.S. Pat. No. 3,488,290 and 3,496,134 and the other patents mentioned therein.

The following examples, in which parts and percentages are by weight unless otherwise stated, are presented to further illustrate the present invention.

EXAMPLE 1

Preparation of
1,3-Bis[(2,2,6,6-tetramethyl-4-piperidylidene)amino]-guanidine

A solution of diaminoguanidine hydrochloride (6.28 grams; 0.05 mole) and 2,2,6,6-tetramethyl-4-piperidone monohydrate (17.3 grams; 0.10 mole) in 200 mls. of ethanol 2B was refluxed for a period of 15 hours while stirring. The resulting slurry was cooled to 25° C and the solid was separated to obtain 10.0 grams of crude 1,3-bis[(2,2,6,6-tetramethyl-4-piperidylidene)amino]-guanidine hydrochloride. Recrystallization of the crude hydrochloride from ethanol 2B gave 8.9 grams of white solid, m.p. 210°-220° C (dec).

A 5 gram sample of the recrystallized hydrochloride was dissolved in 50 mls. of water and a 4% aqueous solution of sodium hydroxide was added thereto until the mixture became alkaline. The solid which precipitated was separated by filtration, washed with water, and dried to obtain 3.2 grams of the free base, m.p. 163°-167° C. Recrystallization of the crude free base from a mixture of benzene and hexane gave 1.0 gram of analytically pure free base, m.p. 164°-166° C.

Analysis: Calculated for $C_{19}H_{37}N_7$ (percent): C, 62.77; H, 10.26; N, 26.97 Found: C, 62,58; H, 10.30; N, 26.84

EXAMPLE 2

Evaluation of Light Stabilization Properties

The product of Example 1 was incorporated at 0.5% by weight into unstabilized polypropylene (Profax 6401) with 0.2% of a processing antioxidant, 2,4,6-tri-t-butylphenol, by dry-blending and milling at 350°-370° F on a standard plastic mill for five minutes, and compression molding the compositions into films (4–5 mils thick) at 400° F. The film was then exposed to light in a Xenon Arc Weather-Ometer (Atlas) until the carbonyl content of the film was increased by 0.10% as determined by infrared spectrophometric measurement. The film required 2800 hours exposure to increase the carbonyl content by 0.10%. A control film identically prepared without the compound of Example 1 required only 400 hours to increase the carbonyl content by 0.10%.

EXAMPLE 3

Preparation of
1,3-Bis[(1,2,2,6,6-pentamethyl-4-piperidylidene)amino]-guanidine

The procedure of Example 1 is used except that 16.94 grams (0.10 mole) of 1,2,2,6,6-pentamethyl-4-piperidone is substituted for the 2,2,6,6-tetramethyl-4-piperidone monohydrate.

Following the procedure of Example 2, substituting 0.5% by weight of the above-mentioned compound for the 1,3-bis[(2,2,6,6-tetramethyl-4-piperidylidene)-amino]guanidine, similar results are obtained.

EXAMPLE 4

Preparation of
1,3-Bis[(1-oxyl-2,2,6,6-tetramethyl-4-piperidylidene)amino]guanidine The procedure of Example 1 is used except that 17.0 grams (0.10 mole) of 1-oxyl-2,2,6,6-tetramethyl-4-piperidone is substituted for the 2,2,6,6-tetramethyl-4-piperidone monohydrate.

EXAMPLE 5

Preparation of
1,3-Bis[(1-hydroxy-2,2,6,6-tetramethyl-4-piperidylidene)amino]guanidine The procedure of Example 1 is used except that 17.1 grams (0.10 mole) of 1-hydroxy-2,2,6,6-tetramethyl-4-piperidone is substituted for the 2,2,6,6-tetramethyl-4-piperidone monohydrate.

EXAMPLE 6

Preparation of
1,3-Bis[(1-n-octyl-2,2,6,6-tetramethyl-4-piperidylidene)amino]guanidine The proceudre of Example 1 is used except that 26.7 grams (0.10 mole) of 1-n-octyl-2,2,6,6-tetramethyl-4-piperidone is substituted for the 2,2,6,6-tetramethyl-4-piperidone monohydrate.

EXAMPLE 7

Preparation of 1,3-Bis[(1-acetyl-2,2,6,6-tetramethyl-4-piperidylidene)amino]guanidine The procedure of Example 1 is used except that 19.7 grams (0.10 mole) of 1-acetyl-2,2,6,6-tetramethyl-4-piperidone is substituted for the 2,2,6,6-tetramethyl-4-piperidone monohydrate.

I claim:

1. A compound of the formula:

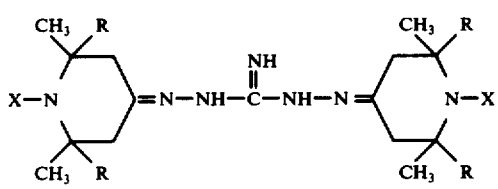

wherein X is —H, —OH, —0., alkyl of 1 to 8 carbon atoms, or carboxylic acyl of 2 to 10 carbon atoms, and R is alkyl of 1 to 8 carbon atoms.

2. A compound according to claim 1 wherein R is methyl.

3. A compound according to claim 2 wherein X is —H.

4. A compound according to claim 2 wherein X is —CH$_3$.

5. A compound according to claim 2 wherein X is —OH.

6. A compound according to claim 2 wherein X is —n—CH$_8$H$_{17}$.

7. A compound according to claim 2 wherein X is

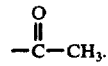

8. A compound according to claim 2 wherein X is —0..

9. A polyolefin stabilized against degradation by ultraviolet light by an effective amount of a compound of claim 1.

10. The composition of claim 9 wherein said effective amount is about 0.1 to about 5% by weight on weight of polyolefin.

11. The composition of claim 10 wherein said effective amount is 0.2 to 2% by weight on weight of polyolefin.

12. The composition of claim 9 wherein said polyolefin is polypropylene.

13. The composition of claim 11 wherein said polyolefin is polypropylene.

* * * * *